United States Patent
Gröger et al.

(10) Patent No.: US 6,987,010 B2
(45) Date of Patent: Jan. 17, 2006

(54) PROCESS FOR THE ENZYMATIC PREPARATION OF ENANTIOMER-ENRICHED β-AMINO ACIDS

(75) Inventors: Harald Gröger, Hanau (DE); Helge Werner, Bruchköbel (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 11/052,243

(22) Filed: Feb. 8, 2005

(65) Prior Publication Data
US 2005/0142646 A1 Jun. 30, 2005

Related U.S. Application Data

(62) Division of application No. 10/430,382, filed on May 7, 2003, now Pat. No. 6,869,781.

(30) Foreign Application Priority Data

May 8, 2002 (DE) ................................ 102 20 739
May 8, 2002 (DE) ................................ 102 20 740

(51) Int. Cl.
    C12P 13/04 (2006.01)
(52) U.S. Cl. ...................... 435/106; 435/197; 435/198; 435/280
(58) Field of Classification Search ................ 435/106, 435/197, 198, 280
    See application file for complete search history.

(56) References Cited

U.S. PATENT DOCUMENTS

| 4,636,470 A | 1/1987 | Empie ......................... 435/280 |
| 5,518,903 A | 5/1996 | Yoshida et al. ............. 435/106 |
| 5,552,317 A | 9/1996 | Houng et al. ............... 435/280 |
| 6,063,615 A | 5/2000 | Stürmer et al. ............. 435/280 |

FOREIGN PATENT DOCUMENTS

| EP | 0 890 649 A1 | 6/1998 |
| WO | WO 98/50575 | 11/1998 |
| WO | WO 01/16090 | 3/2001 |

OTHER PUBLICATIONS

English Language Abstract for EP 0 890 649 A1, Reference AJ1 above.
Abdel-Magid, et al., "Chemical Process Synthesis of β-Amino Acids and Esters," *Current Medicinal Chemistry* 6:955-970 (1999).
Boesch, et al., "An Expedient Method for Resolution of 3-Amino-3-(3'-Pyridyl)Propionic Acid and Related Compounds," *Organic Process Research & Development* 5:23-27 (2001).
Faulconbridge, et al., "Preparation of Enantiomerically Enriched Aromatic β-Amino Acids Via Enzymatic Resolution," *Tetrahedron Lett.* 41:2679-2681 (2000).
Juaristi, et al., "Recent Advances in the Enantioselective Synthesis of β-Amino Acids," *Current Medicinal Chemistry* 6:983-1004 (1999).
Kanerva, et al., "Approach to Highly Enantiopure β-Amino Acid Esters by Using Lipase Catalysis in Organic Media," *Tetrahedron:Asymmetry* 7:1705-1716 (1996).
Katayama, et al., "Enzymatic Resolution of 2-Substituted Tetrahydroquinolines. Convenient Approaches to Tricyclic Quinoxalinediones as Potent NMDA-Glycine Antagonists," *Tetrahedron:Asymmetry* 9:4295-4299 (1998).
Sánchez, et al., "*Candida antarctica* Lipase Catalyzed Resolution of Ethyl (±)-3-Aminobutyrate," *Tetrahedron: Asymmetry* 8:37-40 (1997).
Soloshonok, et al., "An Enzymatic Entry to Enantiopure β-Amino Acids," *Synlett*:339-341 (May 1993).
Soloshonok, et al., "Biocatalytic Resolution of β-Fluoroalkyl-β-Amino Acids," *Tetrahedron:Asymmetry* 5: 1119-1126 (1994).
Soloshonok, et al., "Biocatalytic Approach to Enantiomerically Pure β-Amino Acids," *Tetrahedron:Asymmetry* 7: 1601-1610 (1995).
Database Crossfire/Beilstein 'Online! Beilstein Registry No. 2939300. Jun. 2, 1992, "3-Amino-3-phenyl-propionsäure-propylester" ZP002248822.

*Primary Examiner*—Herbert J. Lilling
(74) *Attorney, Agent, or Firm*—Michael A. Sanzo; Fitch, Even, Tabin & Flannery

(57) ABSTRACT

The present invention relates to processes for the preparation of enantiomerically enriched β-amino acids. The invention also relates to advantageous esters of β-amino acids of the general formula (I)

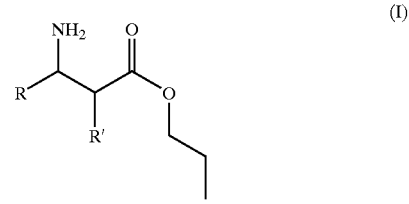

and to the use thereof in the enzymatic preparation of enantiomerically enriched β-amino acids.

14 Claims, No Drawings

PROCESS FOR THE ENZYMATIC PREPARATION OF ENANTIOMER-ENRICHED β-AMINO ACIDS

CROSS REFERENCE TO RELATED APPLICATIONS

The present application is a division of U.S. application Ser. No. 10/430,382, filed on May 7, 2003 now U.S. Pat. No. 6,869,781. The '382 application claims priority to German Application No. 102 20 739.9, filed May 8, 2002, and to German Application No. 102 20 740.2, also filed May 8, 2002. These applications are incorporated in their entirety herein by reference.

FIELD OF THE INVENTION

The present invention relates to processes for the preparation of enantiomerically-enriched β-amino acids and to esters of β-amino acids that can be used for the enzymatic production of enantiomer-enriched preparations.

BACKGROUND OF THE INVENTION

Optically active β-aminocarboxylic acids occur in natural substances such as alkaloids and antibiotics. The isolation of these amino acids is of interest because of their importance as essential intermediates in the preparation of pharmaceuticals (see, e.g., Juaristi, et al., *Curr. Med. Chem.* 6:983–1004 (1999)). Both the free form of optically active β-aminocarboxylic acids and their derivatives have interesting pharmacological effects and can also be used in the synthesis of modified peptides.

Methods for preparing β-aminocarboxylic acids include conventional racemate resolution by means of diastereomeric salts (see e.g., Boesch et al., *Org. Proc. Res. Develop.* 5:23–27 (2001)) and, in particular, the diastereoselective addition of lithium phenylethylamide (Abdel-Magid, et al., *Curr. Med. Chem.* 1999, 6:955–970 (1999)). The latter method has been intensively researched and, despite numerous disadvantages, is generally considered the preferred method of preparation. One of its drawbacks is that, unlike catalytic asymmetrical methods, stoichiometric amounts of a chiral reagent are needed. Expensive and hazardous auxiliary agents, e.g., n-butyllithium, are also needed to activate the stoichiometric reagent by deprotonation. In addition, the reaction must be performed at a low temperature, e.g., approximately −70° C., for satisfactory stereoselectivity, and this imposes restrictions on reactor material, leads to additional costs and entails high energy consumption.

Although biocatalytic methods of preparing optically active β-aminocarboxylic acids have not found widespread use, they offer both economic and ecological advantages. Stoichiometric amounts of a chiral reagent are unnecessary and, instead, small, catalytic amounts of enzymes are used that are natural and environmentally-friendly. Moreover, in contrast to a multiplicity of synthetic metal-containing catalysts, biocatalysts do not require the presence of a metal-containing, and, consequently, toxic feedstock.

The enantioselective N-acylation of β-aminocarboxylic acids has previously been reported. For example, Kanerva et al. describe the enantioselective N-acylation of ethyl esters of various cycloaliphatic β-aminocarboxylic acids with 2,2,2-trifluoroethyl ester in organic solvents using lipase SP 526 from *Candida antarctica* or lipase PS from *Pseudomonas cepacia* as biocatalyst (*Tetrahedron: Asymmetry* 7(6):1707–1716 (1996)).

Sánchez et al. studied the biocatalytic racemate resolution of (±)-ethyl 3-aminobutyrate with lipase from *Candida antarctica* via the preparation of N-acetylated β-aminocarboxylic esters (*Tetrahedron: Asymmetry* 8(1):37–40 (1997)).

EP-A-8 890 649 discloses a process for preparing optically active amino acid esters from a racemic mixture by enantioselective acylation with a carboxylic ester in the presence of a hydrolase selected from the group comprising amidase, protease, esterase and lipase. The unreacted enantiomers of the amino acid esters are subsequently isolated.

WO-A-98/50575 describes a process for obtaining a chiral β-aminocarboxylic acid or its corresponding ester by bringing a racemic β-aminocarboxylic acid, an acyl donor and penicillin G acylase into contact with one another under conditions for stereoselectively acylating one enantiomer of the racemic β-aminocarboxylic acid and under which the other enantiomer is substantially not reacted. A chiral β-aminocarboxylic acid is thus obtained. The reverse reaction sequence has also been studied (Soloshonok, et al., *Synlett:* 339–341 (1993); Soloshonok, et al., *Tetrahedron: Asymmetry* 5:1119–1126 (1994); Soloshonok, et al., *Tetrahedron: Asymmetry* 6:1601–1610 (1995); Cardillo, et al., *Eur. J Org. Chem.* 155–161 (1999)). A disadvantage of this process is that it requires a difficult work-up of the product mixture after enantioselective hydrolysis. After isolating the free β-aminocarboxylic acid, a mixture of phenylacetic acid and N-phenylacetyl-β-aminocarboxylic acid is obtained that is difficult to separate.

A method for obtaining enantiomer-enriched carboxylic acids involves reaction with lipases and, in U.S. Pat. No. 5,518,903, this method was applied to N-protected β-amino acid esters, with varying success. Although the corresponding benzyl ester of racemic N-butoxycarbonyl-β-aminobutyric acid was resolved highly enantioselectively, the remaining methyl esters or n-butyl esters used gave ee values of not more than 70% ee. In this connection, it should be noted that, apparently, going from a methyl ester to a corresponding n-butyl ester is accompanied by an impairment of the ee value of the acid prepared. Thus, starting from the n-butyl ester of N-Boc-β-aminobutyric acid, ester hydrolysis with the enzyme lipase from Asahi results after 8 days in an ee value of the corresponding acid of 45% ee in a yield of 37%. With the lipase PS supplied by Amano, a compound enriched to 61% ee is obtained in the same reaction with a yield of 41% within 7 days. In comparison, the corresponding methyl ester yields 70% ee.

From recently published results it may be inferred that the ester hydrolysis of aromatic β-amino acid ethyl esters at a pH of 8 with the lipase PS supplied by Amano takes place with acceptable yields and very good enantiomeric excesses (Faulconbridge et al., *Tetrahedron Letters* 41:2679–81 (2000)). The product is obtained with an enantiomeric purity of up to 99% ee, but the synthesis, which was performed exclusively in aqueous suspension, is associated with some disadvantages. Although the crystallization is selective under these conditions, the reaction per se results, as documented in Comparison Example 2, in lower ee values, 85.1%. This means a loss in yield due to the formation of the undesirable enantiomer and suggests that ee values may easily also drop below 99% ee or even below 98% ee as a function of slight process fluctuations or because of altered crystallization conditions. An ee value greater than 98% ee, and preferably greater than 99% ee, is, however, often a requirement for pharmaceutical applications. In addition, performance in purely liquid medium would be desirable in order, for example, to be able to ensure good isolation results by means of ultrafiltration. Optimally, a high ee value should likewise be produced in this step.

An enzymatic hydrolysis in the presence of single-phase reaction media using organic solvents was reported by Nagata et al. (*Tetrahedron: Asymmetry* 9:4295–4299 (1998)). In that case, a cyclic β-amino acid ester was used. The best results (enantioselectivities of 94% ee and conversions of 50% with a reaction time of 20 h) were achieved using a solvent mixture composed of acetone (90%) and water (10%). Poorer results were achieved with lower proportions of water. In general, the use of readily water-soluble solvents has proved superior compared with sparingly water-miscible solvents. Thus, diisopropyl ether saturated with water and 20% acetone, produces an ee value of only 58% ee.

SUMMARY OF THE INVENTION

The object of the present invention is to provide improved processes for the enzymatic preparation of β-amino acids. The processes are usable on an industrial scale economically and are particularly good with respect to environmental compatibility, industrial safety, ruggedness of processing, space/time yield and selectivity.

In its first aspect, the invention is directed to a process for producing enantiomer-enriched N-unprotected β-amino acids by the enzymatic hydrolysis of an enantiomeric mixture of N-unprotected β-amino acid esters other than methyl or ethyl esters. The process is, preferably, carried out using β-amino acid alkyl esters or β-amino acid aryl esters. Especially preferred are n-propyl, isopropyl, n-butyl, sec-butyl, isobutyl or tert-butyl esters.

The pH of the process can vary between 4 and 10. Preferably it should be between 6 and 9, and more preferably between 7 and 8.5. The reaction temperature should be between −15° C. and +100° C., preferably between +15° C. and +40° C. and more preferably between +20° C. and +30° C. In a preferred embodiment, the enzyme used is a lipase such as lipase PS from *Pseudomonas cepacia*. In further preferred embodiments, the process is performed in an enzyme membrane reactor and in an aqueous medium optionally containing one or more water-soluble organic solvents. Since there is not a solvent present that forms a distinct organic phase, this process is referred to herein as a "single phase" process or system.

In another aspect, the invention is directed to a β-amino acid n-propyl ester having the following structure (I)

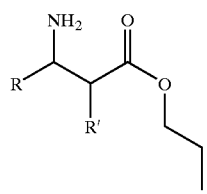

wherein
R represents $(C_1-C_8)$-alkyl, $(C_2-C_8)$-alkenyl, $(C_2-C_8)$-alkynyl, $(C_3-C_8)$-cycloalkyl, $(C_6-C_{18})$-aryl $(C_7-C_{19})$-aralkyl, $(C_3-C_{18})$-heteroaryl, $(C_4-C_{19})$-heteroaralkyl, $((C_1-C_8)$-alkyl$)_{1-3}$-$(C_3-C_8)$-cycloalkyl, $((C_1-C_8)$-alkyl$)_{1-3}$-$(C_6-C_{18})$-aryl, $((C_1-C_8)$-alkyl$)_{1-3}$-$(C_3-C_{18})$-heteroaryl, R' represents H, $(C_1-C_8)$-alkyl, $(C_2-C_8)$-alkenyl, $(C_2-C_8)$-alkynyl, $(C_3-C_8)$-cycloalkyl, $(C_6-C_{18})$-aryl, $(C_7-C_{19})$-aralkyl, $(C_3-C_{18})$-heteroaryl, $(C_4-C_{19})$-heteroaralkyl, $((C_1-C_8)$-alkyl$)_{1-3}$-$(C_3-C_8)$-cycloalkyl, $((C_1-C_8)$-alkyl$)_{1-3}$-$(C_6-C_{18})$-aryl, $((C_1-C_8)$-alkyl$)_{1-3}$-$(C_3-C_{18})$-heteroaryl.

The invention also includes a process for producing enantiomer-enriched N-unprotected β-amino acids by enzymatically hydrolyzing an enantiomeric mixture of N-unprotected β-amino acid n-propyl esters having a structure defined by formula I as described above. The process is preferably performed at a pH of between 6 and 9, and more preferably at between 7 and 8.5. The reaction temperature is preferably between +15° C. and +40° C. and more preferably between +20° C. and +30° C. The hydrolysis reaction may be carried out with a lipase, in an aqueous medium, optionally containing a water-soluble organic solvent. The esters should also be useful in the two phase system described below In another aspect, the invention is directed to a process for producing enantiomer-enriched N-unprotected β-amino acids by the enzymatic hydrolysis of an enantiomeric mixture of N-unprotected β-amino acid esters where hydrolysis takes place in a system having an aqueous phase comprising water and an organic phase comprising an organic solvent. This "two-phase" process may be carried out using open-chain β-amino acid esters with β-amino acid alkyl esters or β-amino acid aryl esters being preferred. Especially preferred are n-propyl, isopropyl, n-butyl, sec-butyl, isobutyl or tert-butyl esters. Unlike the single phase process described above, the two phase process may be efficiently carried out using either methyl esters or ethyl esters (although these compounds are not the most preferred).

As with the single phase process, the pH of the two phase process should be between 4 and 10, preferably between 6 and 9, and more preferably between 7 and 8.5. Preferred reaction temperature is between −15° C. and +100° C., more preferably between +15° C. and +40° C. and still more preferably between +20° C. and +30° C. The most preferred enzyme is a lipase such as lipase PS from *Pseudomonas cepacia*. The process may advantageously be performed in an enzyme membrane reactor with ethers, ketones, esters, saturated or unsaturated linear or branched-chain hydrocarbons used as the organic solvent.

It has been found that the two phase process has a high reactivity and results in good enantioselectivity. The system can be optimized in such a way that product is produced at ≧99% ee. When reactions are performed using ethyl esters, the ee value in accordance with Example 5 (89% ee) was found to be markedly better than that obtained when the reaction is carried out in a single phase aqueous system (see Examples 1 and 2). In addition to the processing advantages of organic solvents, this process has the advantage of generating higher enantioselectivities in the products compared to that obtained in aqueous medium. Whether, the single phase system or the two phase system is preferable in a particular situation will depend factors that include that needs of the manufacturer and the availability of esters, enzymes and solvents. The advantages of each process are discussed further below.

DETAILED DESCRIPTION OF THE INVENTION

A. Esters

As discussed above the invention includes P-amino acid n-propyl esters having the following structure (I)

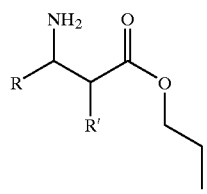

(I)

wherein

R represents $(C_1–C_8)$-alkyl, $(C_2–C_8)$-alkenyl, $(C_2–C_8)$-alkynyl, $(C_3–C_8)$-cycloalkyl, $(C_6–C_{18})$-aryl, $(C_7–C_{19})$-aralkyl, $(C_3–C_{18})$-heteroaryl, $(C_4–C_{19})$-heteroaralkyl, $((C_1–C_8)$-alkyl$)_{1-3}$-$(C_3–C_8)$-cycloalkyl, $((C_1–C_8)$-alkyl$)_{1-3}$-$(C_6–C_{18})$-aryl, $((C_1–C_8)$-alkyl$)_{1-3}$-$(C_3–C_{18})$-heteroaryl, R' represents H, $(C_1–C_8)$-alkyl, $(C_2–C_8)$-alkenyl, $(C_2–C_8)$-alkynyl, $(C_3–C_8)$-cyclalkyl, $(C_6–C_{18})$-aryl, $(C_7–C_{19})$-aralkyl, $(C_3–C_{18})$-heteroaryl, $(C_4–C_{18})$-heteroaralkyl, $((C_1–C_8)$-alkyl$)$-$_{1-3}$-$(C_3–C_8)$-cycloalkyl, $((C_1–C_8)$-alkyl$)_{1-3}$-$(C_6–C_{18})$-aryl, $((C_1–C_8)$-alkyl$)_{1-3}$-$(C_3–C_{18})$-heteroaryl.

Particularly preferred compounds are those in which R represents an aromatic radical, especially phenyl, thienyl, furyl, pyridyl, and the derivatives thereof mono- or polysubstituted on the aromatic ring, especially with $(C_1–C_8)$-alkyl or $(C_1–C_8)$-alkoxy as substituents and in which R' represents H. 3-amino-3-phenylpropionic acid n-propyl ester may be mentioned as one such compound that is of particular interest.

B. Preferred Compounds for Single Phase Process

In one aspect the present invention is directed to a single phase process for the preparation of enantiomerically enriched N-unprotected β-amino acids by enzymatic hydrolysis and which utilizes any of the compounds shown above in section A. This process differs from previously described methods in that neither methyl nor ethyl N-unprotected β-amino acid esters are used. It was found that surprisingly improved results are obtained, both in terms of the space/time yield and in terms of selectivity, when bulkier ester groups having, for example, $(C_3–C_8)$-alkyl radicals are used for the enzymatic hydrolysis (compare Examples 1 and 2 below with Examples 3 and 4). The results obtained using the present process are surprising in view of U.S. Pat. No. 5,518,903 discussed above and because, with a more rapid reaction, the probability of enantio-differentiation generally decreases. For example generally lower enantio-selectivities have been found to occur at higher reaction temperatures.

C. Preferred Compounds for Two Phase Process

In a second aspect present invention is directed to a process similar to that described above but which is performed in a two-phase system composed of water and an organic solvent. Preferred compounds are those of general Formula (II)

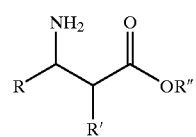

(II)

where

R, and R" denote, independently of one another, $(C_1–C_8)$-alkyl, $(C_2–C_8)$-alkenyl, $(C_2–C_8)$-alkynyl, $(C_3–C_8)$-cycloalkyl, $(C_6–C_{18})$-aryl, $(C_7–C_{19})$-aralkyl, $(C_3–C_{18})$-heteroaryl, $(C_4–C_{19})$-heteroaralkyl, $((C_1–C_8)$-alkyl$)_{1-3}$-$(C_3–C_8)$-cycloalkyl, $((C_1–C_8)$-alkyl$)_{1-3}$-$(C_6–C_{18})$-aryl, and $((C_1–C_8)$-alkyl$)_{1-3}$-$(C_3–C_{18})$-heteroaryl, and R' denotes H, $(C_1–C_8)$-alkyl, $(C_2–C_8)$-alkenyl, $(C_2–C_8)$-alkynyl, $(C_3–C_8)$-cycloalkyl, $(C_6–C_{18})$-aryl, $(C_7–C_{19})$-aralkyl, $(C_3–C_{18})$-heteroaryl, $(C_4–C_{19})$-heteroaralkyl, $((C_1–C_8)$-alkyl$)_{1-3}$-$(C_3–C_8)$-cycloalkyl, $((C_1–C_8)$-alkyl$)_{1-3}$-$(C_6–C_{18})$-aryl, and $((C_1–C_8)$-alkyl$)_{1-3}$-$(C_3–C_{18})$-heteroaryl.

D. Process Conditions and Parameters

Unless otherwise indicated, the conditions and preferred parameters described below refer to both the single phase and two phase processes. A person skilled in the art is free to choose an appropriate ester group for use in the process and will base the selection on economic and chemical factors. Favourable alcohols for forming esters are, in particular, those that can easily be removed from the reaction mixture, e.g., by distillation. These include alkyl alcohols or aryl alcohols, optionally low-boiling phenol or benzyl alcohol. The β-amino acid alkyl esters or β-amino acid aryl esters obtainable with these alcohols are therefore preferably used in the hydrolysis. Very particular preference is given to the use of corresponding n-propyl, isopropyl, n-butyl, sec-butyl, isobutyl or tert-butyl esters of the β-amino acids.

The choice of reaction parameters is also largely discretionary and appropriate conditions can be found using methods well known and routine in the art. As a guideline, the pH value range of the reaction should be between 4 and 10, preferably between 6 and 9 and more preferably between 7 and 8.5; The enzyme used for hydrolysis is preferably a lipase. The PS lipase supplied by Amano has proven to be particularly suitable at a pH of about 8.

Optimum temperature can be determined on a case by case basis depending on the enzyme selected. For enzymes from thermophilic organisms, temperatures of up to 100° C. are possible. In contrast, other enzymes work best at <0° C. to −15° C., possibly in an ice matrix. In most cases, however, the reaction temperature should preferably be in the range of between 15 and 40° C. and, more preferably, between 20 and 30° C.

One of skill in the art will choose an enzyme for use in reactions based upon their particular needs and objectives. Many suitable enzymes are known and can be selected, for example, from *Enzyme Catalysis in Organic Synthesis*, (ed. K. Drauz, H. Waldmann, VCH, 1995, page 165) and from the literature cited therein. Preferably, a lipase is used for the ester hydrolysis, with the lipase PS from *Pseudomonas cepacia* being particularly preferred. The enzyme can be used in free form as a homogeneously purified compound from either a natural or recombinant source. It may be used as a constituent of an intact guest organism or in conjunction with the digested cell material of the host organism purified to the extent desired.

The use of an immobilized enzyme is also an option (see, e.g., Sharma, et al., *Angew Chem.* 94:836–852 (1982)). Advantageously, immobilization takes place through lyophilization (Paradkar, et al., *J. Am. Chem. Soc.* 116:5009–5010 (1994); Mori, et al., *Tetrahedron Lett.* 38,1971–1974 (1997); Otamiri, et al., *Biocatalysis* 6:291–305 (1992)). Particularly preferred is lyophilization in the presence of surfactant substances, such as Aerosol OT or polyvinylpyrrolidone or polyethylene glycol (PEG) or Brij 52 (diethylene glycol monocetyl ether) (Kamiya, et al.,

*Biotechnol. Tech.* 11:375–378 (1997)). Especially preferred is immobilization on Eupergit®, in particular Eupergit C®, and Eupergit 250® (Röhm) (see, Katchalski-Katzir, et al, *Mol. Catal. B: Enzym.* 10:157 (2000)). Equally preferred is immobilization on Ni-NTA in combination with the polypeptide modified by attaching a His tag (Hexahistidine) (Petty, "Metal-chelate affinity chromatography," In: Ausubel, et al. eds. *Current Protocols in Molecular Biology*, vol. 2, New York: John Wiley and Sons (1996)). Alternatively, enzymes may be used as cofactor-bound cross-linked enzyme crystals (CLECs) (see, St. Clair, et al., *Angew. Chem. Int. Ed.* 39:380–383 (2000)). These measures can make it possible to generate, from polypeptides that are unstable in organic solvents, those that can function in mixtures of aqueous and organic solvents or entirely in an organic medium.

The reactions of the present invention can be performed in any reaction vessel provided for the purpose. These include normal batch reactors, loop reactors or enzyme membrane reactors (Bommarius, et al., "Membrane Bioreactors for the Production of Enantiomerically Pure α-Amino Acids," In: *Chirality in Industry*, Collins, et al., eds., John Wiley & Sons, pages 371–397 (1992).

If enzymes are used that exist in adsorbed form, for example on water-insoluble support materials and/or with minor constituents or stabilizers, it will be advantageous, when practical, to isolate the enzyme from the insoluble support and/or minor constituents or stabilizers prior to use in the reaction. This will help prevent potential contamination of the product produced. For example, the lipase PS supplied by Amano is absorbed on silica supports. In this case, the aqueous enzyme solution can be filtered prior to adding the reactants to the medium in order to remove the silicic acids from the reaction system. The activity of enzymes is not, as a rule, adversely affect by this procedure.

Apart from the differences in the choice of ester compounds discussed above, the main difference between the single phase and two phase processes will be in the solvents used. When using the single phase system, the esters in the reaction may sometimes exhibit poor solubility in an aqueous reaction medium. In such cases it may be advantageous, depending on the solvent tolerance of the particular enzymes used, to add water-soluble organic solvents to the reaction mixture in order to obtain a homogeneous reaction phase. Suitable water-soluble organic solvents include, inter alia: acetone, DMF, ethanol and methanol. However, the reaction is also possible at higher substrate concentrations with the formation of a suspension.

When using the two phase process, any organic solvent that forms two phases with water under the given reaction conditions is compatible with the present invention. This includes all the types of organic, insoluble or poorly water-soluble solvents and mixtures thereof. Examples include, ethers, ketones, esters, and saturated or unsaturated, linear or branched-chain hydrocarbons. In this regard, methyl-tert-butyl ether (MTBE), diisopropyl ether, ethyl acetate, hexane, heptane, cyclohexane, methylcyclohexane and toluene, and mixtures of these solvents may be used.

E. Definitions

A "two phase process" or "two phase system" as used herein refers to a procedure in which both an aqueous phase and a distinct organic phase are formed. In a "single phase system" or "single phase process" there is not separate organic and aqueous phases. However, it should be recognized that a single phase may not necessarily constitute a solution. For example, a single phase may take the form of a homogeneous suspension.

For the purposes of the present invention, the term "N-unprotected" means that the β-nitrogen atom of the acid is not blocked by an N-protective group that is stable under the reaction conditions. Common protective include Z, Boc, Fmoc, Eoc, Moc, acetyl, etc.

To be regarded as $(C_1-C_8)$-alkyl are methyl, ethyl, n-propyl, isopropyl, n-butyl, isobutyl, sec-butyl, tert-butyl, pentyl, hexyl, heptyl or octyl together with all the bonding isomers. These may be singly or multiply substituted by $(C_1-C_8)$-alkoxy, $(C_1-C_8)$-haloalkyl, OH, halogen, $NH_2$, $NO_2$, SH or S-$(C_1-C_8)$-alkyl. $(C_3-C_8)$-alkyl is to be regarded in a similar manner.

$(C_2-C8)$-alkenyl is to be understood as meaning a $(C_1-C_8)$-alkyl radical as described above, with the exception of methyl, containing at least one double bond.

$(C_2-C_8)$-aklynyl is to be understood as meaning a $(C_1-C_8)$-alkyl radical as described above, with the exception of methyl, containing at least one triple bond.

$(C_1-C_8)$-acyl is to be understood as meaning a $(C_1-C_8)$-alkyl radical bonded to the molecule by means of a —C=O group.

$(C_3-C_8)$-cycloalkyl is to be understood as meaning cyclopropyl, cyclobutyl, cyclopentyl, cyclohexyl or cycloheptyl radicals, etc. These may be substituted by one or more halogens and/or N-, O-, P-, S-atom-containing radicals and/or may have N-, O-, P-, S-atom-containing radicals in the ring, such as, for example, 1-, 2-, 3-, 4-piperidyl, 1-, 2-, 3-pyrrolidinyl, 2-, 3-tetrahydrofuryl, 2-, 3-, 4-morpholinyl. These may be singly or multiply substituted by $(C_1-C_8)$-alkoxy, $(C_1-C_8)$-haloalkyl, OH, halogen, $NH_2$, $NO_2$, SH, S-$(C_1-C_8)$-alkyl, $(C_1-C_8)$-acyl, $(C_1-C_8)$-alkyl.

A $(C_6-C_{18})$-aryl radical is understood as meaning an aromatic radical containing 6 to 18 carbon atoms. Examples include phenyl, naphthyl, anthryl, phenanthryl, biphenyl radicals. These radicals may be singly or multiply substituted by $(C_1-C_8)$-alkoxy, $(C_1-C8)$-haloalkyl, OH, halogen, $NH_2$, $NO_2$, SH, S-$(C_1-C_8)$-alkyl, $(C_1-C_8)$-acyl, $(C_1-C_8)$-alkyl.

A $(C_7-C_{19})$-aralkyl radical is a $(C_6-C_{18})$-alkyl radical bonded to the molecule by means of a $(C_1-C_8)$-alkyl radical.

$(C_1-C_8)$-alkoxy is a $(C_1-C_8)$-alkyl radical bonded to the molecule under consideration by means of an oxygen atom.

$(C_1-C_8)$-alkoxycarbonyl is a $(C_1-C_8)$-alkyl radical bonded to the molecule under consideration by means of an —OC(O) group. The same applies analogously to the other oxycarbonyl radicals.

$(C_1-C_8)$-haloalkyl is a $(C_1-C_8)$-alkyl radical substituted by one or more halogen atoms.

As used herein, $(C_3-C_{18})$-heteroaryl radical denotes a five-, six- or seven-member aromatic ring system containing 3 to 18 carbon atoms and that contains one or more heteroatoms, such as, for example, nitrogen, oxygen or sulphur in the ring. Examples of such heteroaromatics are, in particular, radicals, such as 1-, 2-, 3-furyl, 1-, 2-, 3-pyrrolyl, 1-,2-,3-thienyl, 2-, 3-, 4-pyridyl, 2-, 3-, 4-, 5-, 6-, 7-indolyl, 3-, 4-, 5-pyrazolyl, 2-,4-, 5-imidazolyl, acridinyl, quinolinyl, phenanthridinyl, and 2-, 4-, 5-, 6-pyrimidinyl. These may be singly or multiply substituted by $(C_1-C_8)$-alkoxy, $(C_1-C_8)$-haloalkyl, OH, halogen, $NH_2$, $NO_2$, SH, S-$(C_1-C_8)$-alkyl, $(C_1-C_8)$-acyl, $(C_1-C8)$-alkyl.

$(C_4-C_{19})$-heteroaralkyl is to be understood as meaning a heteroaromatic system corresponding to the $(C_7-C_{19})$-aralkyl radical described above.

Examples of suitable as halogens are fluorine, chlorine, bromine and iodine.

As used herein, the term "enantiomer-enriched" means that an enantiomer, relative to its optical antipodes, constitutes >50% and <100% of a mixture.

Unless otherwise indicated, the structures shown refer to all possible diastereomers and enantiomers and their mixtures that are possible.

EXAMPLES

Comparison Example 1

Single Phase Reaction Using Ethyl Ester 9.2 mmol of the racemic compound rac-3-amino-3-phenylpropionic acid ethyl ester (1.79 g) are taken up in 50 ml of water, and the solution is adjusted to a pH value of pH 8.2 by means of automatic pH metering by addition of 1 M sodium hydroxide solution (obtained from Merck). In order to dissolve the ester without residue, 3 ml of acetone are also added. When a reaction temperature of 20° C. is reached, 200 mg of Amano Lipase PS (Pseudomonas cepacia; obtained from Amano Enzymes, Inc.) are added in order to start the reaction. After a reaction time of 3 and 6 hours, the rate of conversion and, after 6 hours, the enantioselectivity of the resulting (S)-3-amino-3-phenylpropionic acid are determined. A conversion of 18.5% after 3 hours and 37.8% after 6 hours and an enantioselectivity of 85.1% ee (after 6 hours) are determined. The conversion and enantioselectivity were determined by HPLC.

Comparison Example 2

Second Single Phase Reaction Using Ethyl Ester 9.2 mmol of the racemic compound ethyl rac-3-amino-3-phenylpropionate (1.79 g) are taken up in 50 ml of a solvent mixture composed of 25 ml of water and 25 ml of acetone as organic solvent. The solution is set to a pH of 8.2 by means of automatic pH adjustment through adding 1 M sodium hydroxide solution (obtained from Merck). On reaching a reaction temperature of 20° C., 200 mg of lipase PS (Pseudomonas cepacia; obtained through Amano Enzymes, Inc.) are added to start the reaction. After a reaction time of 3, 5 and 24 hours, the conversion rate of the (S)-3-amino-3-phenylpropionic acid formed is determined. A conversion of 1.8% after 3 hours, 2.0% after 5 hours and 5.5% after 24 hours is determined. The value of the enantioselectivity was not determined because of the unsatisfactory course of the reaction in view of the low conversion. The conversion is determined by means of HPLC.

Example 3

Single Phase Reaction Using n-Propyl Ester 9.2 mmol of the racemic compound rac-3-amino-3-phenylpropionic acid n-propyl ester (1.91 g) are taken up in 50 ml of water, and the solution is adjusted to a pH value of pH 8.2 by means of automatic pH metering by addition of 1 M sodium hydroxide solution (obtained from Merck). In order to dissolve the ester without residue, 3 ml of acetone are also added for dissolution. When a reaction temperature of 20° C. is reached, 200 mg of Amano Lipase PS (Pseudomonas cepacia; obtained from Amano Enzymes, Inc.) are added in order to start the reaction. After a reaction time of one hour, the rate of conversion and, after 3 hours, the enantioselectivity of the resulting (S)-3-amino-3-phenyl-propionic acid are determined. A conversion of 48.7% after one hour and an enantioselectivity of 96.4% ee (after 3 hours) are determined. The conversion and enantioselectivity were determined by HPLC.

Example 4

Single Phase Reaction Using n-Butyl Ester 8.63 mmol of the racemic compound rac-3-amino-3-phenylpropionic acid n-butyl ester (1.91 g) are taken up in 50 ml of water, and the solution is adjusted to a pH value of pH 8.2 by means of automatic pH metering by addition of 1 M sodium hydroxide solution (obtained from Merck). In order to dissolve the ester without residue, 3 ml of acetone are also added for dissolution. When a reaction temperature of 20° C. is reached, 200 mg of Amano Lipase PS (Pseudomonas cepacia; obtained from Amano Enzymes, Inc.) are added in order to start the reaction. After a reaction time of 3 hours, both the rate of conversion and the enantioselectivity of the resulting (S)-3-amino-3-phenylpropionic acid are determined. A conversion of 45.2% and an enantioselectivity of 96.8% ee are determined. The conversion and enantioselectivity were determined by HPLC.

Example 5

Two Phase Reaction Using Ethyl Ester 9.2 mmol of the racemic compound ethyl rac-3-amino-3-phenylpropionate (1.79 g) are taken up in 50 ml of a two-phase solvent mixture composed of 25 ml of water and 25 ml of methyl tert-butyl ether (MTBE) as the organic solvent component and set to a pH of 8.2 by automatic pH adjustment through adding 1 M sodium hydroxide solution (obtained through Merck). On reaching a reaction temperature of 20° C., 200 mg of lipase PS (Pseudomonas cepacia; obtained through Amano Enzymes, Inc.) are added to start the reaction. After a reaction time of 3, 5 and 24 hours, the conversion rate of the (S)-3-amino-3-phenylpropionic acid formed is determined. A conversion of 23.5% after 3 hours or a quantitative conversion of approximately 50% after 15 hours and an enantioselectivity of 89.0% ee (after 15 hours) are determined. The conversion and enantioselectivity are determined by means of HPLC.

Example 6

Two Phase Reaction Using n-Propyl Ester 81 ml of water are placed in a vessel, and 1.45 g of Amano Lipase PS (Pseudomonas cepacia; obtained through Amano Enzymes, Inc.) are added thereto. The undissolved solid is then filtered off. 81 ml of methyl tert-butyl ether (MTBE) as organic solvent are added to the aqueous enzyme solution obtained as filtrate. The resulting two-phase system is adjusted to pH 8.2 by means of automatic pH metering by addition of 1 M sodium hydroxide solution (obtained through Merck). When a temperature of 20° C. is reached, 188.2 mmol of the racemic compound rac-3-amino-3-phenylpropionic acid n-propyl ester (39.0 g) are added, and the reaction is started. The reaction time is 15 hours, during which a white precipitate consisting of the desired product (S)-3-amino-3-phenyl-propionic acid forms. After a reaction time of 15 hours, 160 ml of acetone are added to complete the precipitation, stirring is then carried out for about 45 minutes, and the solid is filtered off. The solid is washed several times with a small amount of acetone and is then dried in vacuo. 12.91 g of the desired (S)-3-amino-3-phenylpropionic acid are obtained, corresponding to a yield of 41.6%. The enantioselectivity for the product is 99.6% ee. The enantioselectivity was determined by HPLC. The chemical purity was determined as 98.8% (determined by titration). The structure of the product was additionally confirmed by NMR spectroscopy.

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A process for producing enantiomer-enriched N-unprotected β-amino acids, comprising enzymatically hydrolyzing an enantiomeric mixture of N-unprotected β-amino acid esters with a hydrolase, wherein the hydrolysis takes place in a two-phase system, and wherein said two-phase system has an aqueous phase comprising water and an organic phase comprising an organic solvent.

2. The process of claim 1, wherein said N-unprotected β-amino acid esters are open-chain β-amino acid esters.

3. The process of claim 1, wherein said N-unprotected β-amino acid esters are β-amino acid alkyl esters or β-amino acid aryl esters.

4. The process of claim 3, wherein said N-unprotected β-amino acid esters are n-propyl, isopropyl, n-butyl, sec-butyl, isobutyl or tert-butyl esters.

5. The process according any one of claims 1–4, wherein the pH of the reaction is between 4 and 10.

6. The process of claim 5, wherein said pH is between 6 and 9.

7. The process of claim 6, wherein said pH is between 7 and 8.5.

8. The process any one of claims 1–4, wherein the temperature during the reaction is between −15° C. and +100° C.

9. The process of claim 8, wherein said temperature is between +15° C. and +40° C.

10. The process of claim 9, wherein said temperature is between +20° C. and +30° C.

11. The process of any one of claims 1–4 wherein said enzymatic hydrolysis is carried out with a lipase.

12. The process of claim 11, wherein said lipase is the lipase PS from *Pseudomonas cepacia*.

13. The process of any one of claims 1–4, wherein hydrolysis is performed in an enzyme membrane reactor.

14. The process of anyone of claims 1–4, wherein said organic solvent is selected from the group consisting of: an ether; ketone; ester; and a saturated or unsaturated linear or branched-chain hydrocarbon.

* * * * *